United States Patent [19]

Weiner et al.

[11] Patent Number: 4,694,827
[45] Date of Patent: Sep. 22, 1987

[54] INFLATABLE GASTRIC DEVICE FOR TREATING OBESITY AND METHOD OF USING THE SAME

[76] Inventors: Brian C. Weiner; Sarah H. Weiner, both of 24 Bowling Green Pl., Staten Island, N.Y. 10314

[21] Appl. No.: 818,736

[22] Filed: Jan. 14, 1986

[51] Int. Cl.⁴ ............................................ A61B 17/00
[52] U.S. Cl. ................................ 128/303 R; 128/344
[58] Field of Search ............... 128/344, 348.1, 303 R, 128/345, 1 R; 604/96

[56] References Cited

U.S. PATENT DOCUMENTS

| 766,336 | 8/1904 | Farrington | 128/344 |
| 797,676 | 8/1905 | Flowers | 128/344 |
| 4,416,267 | 11/1983 | Garren et al. | 128/1 R |

*Primary Examiner*—Michael H. Thaler
*Attorney, Agent, or Firm*—Cooper, Dunham, Griffin & Moran

[57] ABSTRACT

A balloon insertable and inflatable in the stomach to deter ingestion of food and having, when inflated, a plurality of smooth-surfaced convex protrusions disposed to permit engagement of the stomach wall by the balloon only at spaced localities, for minimizing mechanical trauma of the stomach wall by the balloon.

10 Claims, 5 Drawing Figures

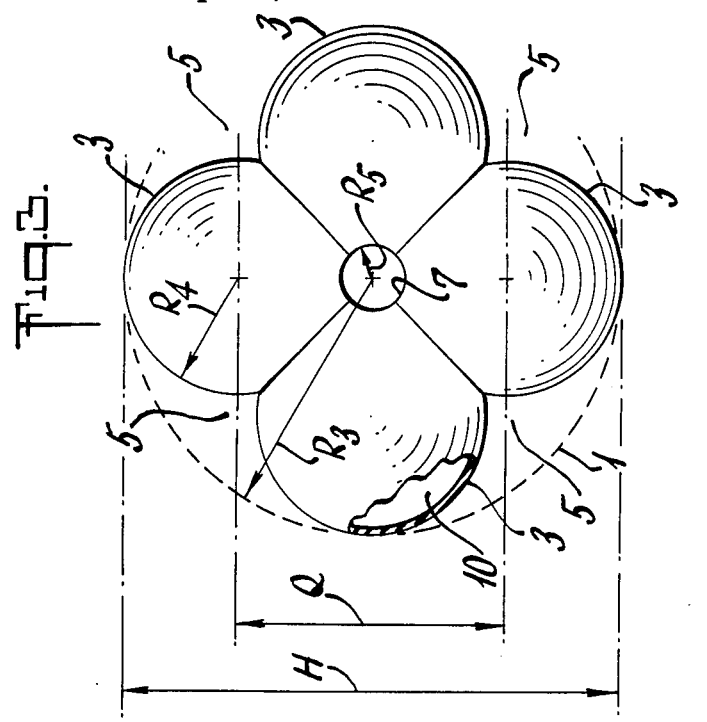
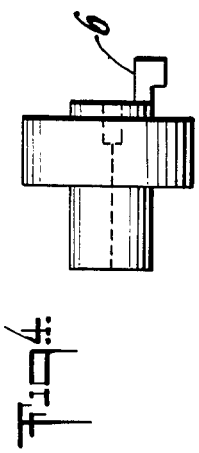
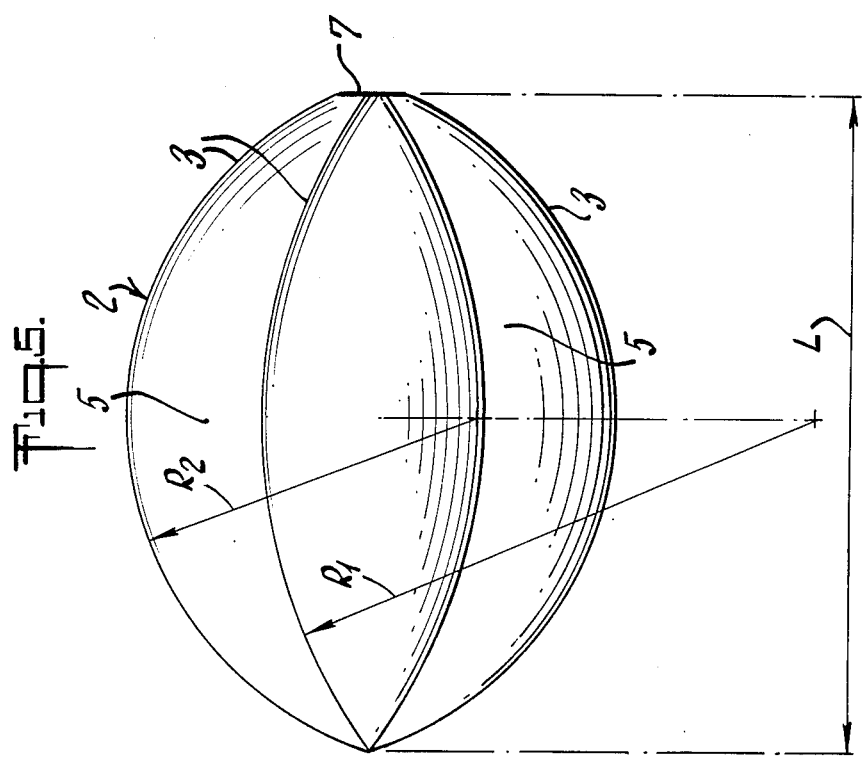

INFLATABLE GASTRIC DEVICE FOR TREATING OBESITY AND METHOD OF USING THE SAME

BACKGROUND OF THE INVENTION

This invention relates to inflatable devices for insertion in the stomach of a human or other animal to control obesity.

Various treatments for the illness of obesity have been employed. Each treatment differs in degree of effectiveness as well as undesirable side effects.

Pyschiatric or dietary regimens depend upon the will power of the patient to achieve the desired results. While weight loss may occur, the lack of will power in patients often leads to failure in the end result.

Surgical treatment of obesity is another approach to the problem. The various attempts have included gastric bypasses, small-bowel bypasses and other procedures. While more effective than psychiatric or dietary regimens, surgical treatments have often resulted in serious physiologic and metabolic derangements.

Devices have been developed which reduce the resevoir capacity of the stomach to achieve early satiety. Inflatable bag and tube combinations have been proposed wherein the bag is swallowed into the stomach. U.S. Pat. No. 4,133,315 discloses such a combination. The tubing remains attached to the bag and inside the esophagus of the person being treated. The bag is periodically inflated, particularly just prior to mealtime or during the meal. Once the person has eaten, the bag can be deflated.

U.S. Pat. No. 4,246,893 discloses an inflatable bag and tube combination which is surgically positioned outside and adjacent to the stomach. Upon inflation of the bag the upper abdomen is distended and the stomach compressed to thereby produce a sense of satiety which reduces the person's desire to ingest food.

U.S. Pat. No. 4,416,267 discloses a device which reduces the size of the gastric compartment and which is easily removed. The ballon is inflated to approximately 80% of the stomach volume and remains in the stomach for a period of perhaps 3 months or more. The balloon has a central opening serving as a passageway through the stomach for both liquids and solids.

U.S. Pat. No. 4,485,805 discloses a balloon type weight loss device which can be placed in a person's stomach through the mouth and esophagus without great discomfort. The structure used to place the balloon is entirely removed once the balloon is properly installed so that the balloon alone remains in the stomach.

The prior art fails to address the problem of potential deleterious contact with the gastric mucosa which can result from leaving an inflated bag in the stomach for an extended period of time. Additionally, most designs do not adequately provide passageways for food and gastric secretions.

SUMMARY OF THE INVENTION

The present invention contemplates a flexible-walled balloon which is insertable and inflatable within the stomach of an animal to deter ingestion of food by occupying a substantial portion of the stomach volume. The balloon has a plurality of wall portions that form smooth-surfaced convex outward protrusions when inflated. The protrusions are distributed around the periphery of the balloon and cooperatively define a plurality of outwardly open channels for passage of fluent material between the balloon outer surface and the stomach wall. The protrusions are shaped and disposed to permit engagement of the stomach wall by the balloon only at spaced localities so as to maintain a substantial portion of the stomach wall away from contact with the balloon.

The balloon's protrusions may be shaped to engage the stomach wall substantially only tangentially and to maintain the stomach wall away from contact with the balloon surface except at localities of tangential engagement of the stomach wall by these protrusions.

The balloon's protrusions may be lobes extending longitudinally between first and second diametrically opposed localities on the inflated balloon, where the channels are valleys defined between adjacent lobes.

The balloon may have a generally elongated shape. Each lobe may extend lengthwise of the balloon.

The balloon's protrusions may be distributed substantially uniformly around an axis of the balloon extending between the diametrically spaced localities. They may be identical in dimension and configuration. They may taper toward each of the diametrically spaced localities.

The balloon may contain four protrusions disposed 90° apart around the axis.

The balloon may have at one end a self-sealing hole through which a hollow pin can be introduced, the pin being constructed so as to be compatible with air delivery through the main "air" port on a standard upper endoscope. A tag of plastic may be attached at the hole so the balloon can be held by a standard endoscopic biopsy forceps. The balloon may be flexible and narrow enough to pass through the small bowel if deflated.

The balloon described above diminishes the surface area of the device touching the gastric mucosa. It also allows an unobstructed pathway for the passage of food and gastric secretions to the small intestine.

Further features and advantages of the invention will be apparent from the detailed description hereinbelow set forth, together with the accompanying drawings.

BRIEF DESCRIPTION OF THE DRAWINGS

FIG. 3 is an end view of the balloon fully inflated.

FIG. 4 is a schematic side view of the valve port and plastic tag.

FIG. 5 is a plan view of a balloon in an inflated condition.

DETAILED DESCRIPTION

Figure 1:
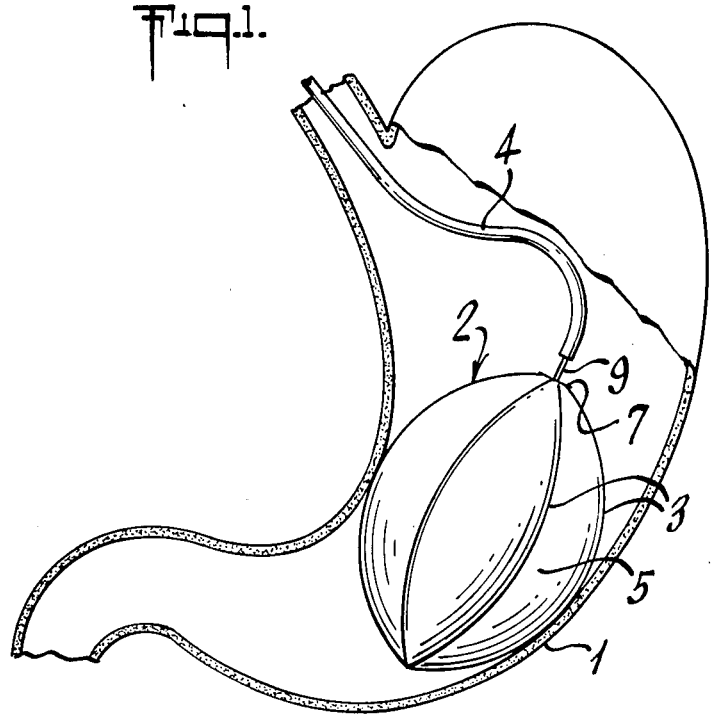
FIG. 1 is a schematic side view illustrating the balloon fully inflated within the stomach and attached to the insufflation tube.

Referring in more particularity to the drawings, the several figures herein illustrate a stomach implant or insert for treating obesity in humans by reducing the stomach volume. Specifically, the stomach insert is an inflatable balloon 2 having a plurality of smooth-surfaced convex outward protrusions 3 (four being shown) which cooperatively form a plurality of outwardly open channels 5. The device is constructed of a suitable acid resistant, pepsin resistant rubbery, flexible and durable film such that the balloon is capable of holding a charge of air when the balloon rests inside the stomach.

The channels 5 provide a passageway for solids and liquids as they pass through the stomach cavity. As best shown in FIG. 3, the channels 5 are positioned between the protrusions 3.

The protrusions 3 perform a dual function of forming the channels 5, as well as maintaining a substantial portion of the stomach wall away from contact with the balloon 2.

In an exemplary embodiment, the balloon 2 fills a potential volume of approximately 500 cubic centimeters, having a diameter of 7–8 centimeters and a long axis of 10–11 centimeters. The balloon pressure is higher than average intragastric pressure during digestion to maintain shape, but less than maximal pressure generated by the stomach contractions, to eliminate mucosal damage.

At one end of the balloon 2 is a self-sealing hole 7 through which a hollow pin 9 can be introduced. Prior to positioning the balloon inside the stomach, an insufflation tube 4 is attached to the deflated balloon. The insufflation tube carries the hollow pin which extends into the balloon through the self-sealing hole.

The inflated balloon is positioned as shown in FIG. 1 with the lobes forming channels serving as a passageway through the stomach for both liquids and solids. The protrusions reduce the amount of surface area which contacts the stomach wall (engaging the gastric mucosa essentially only tangentially), thereby reducing the deleterious effects resulting from excessive contact with the gastric mucosa. The balloon remains in the stomach for the period the person is being treated for obesity, and it reduces the volume size of the stomach thereby curbing the appetite of the person being treated for obesity.

Figure 2:
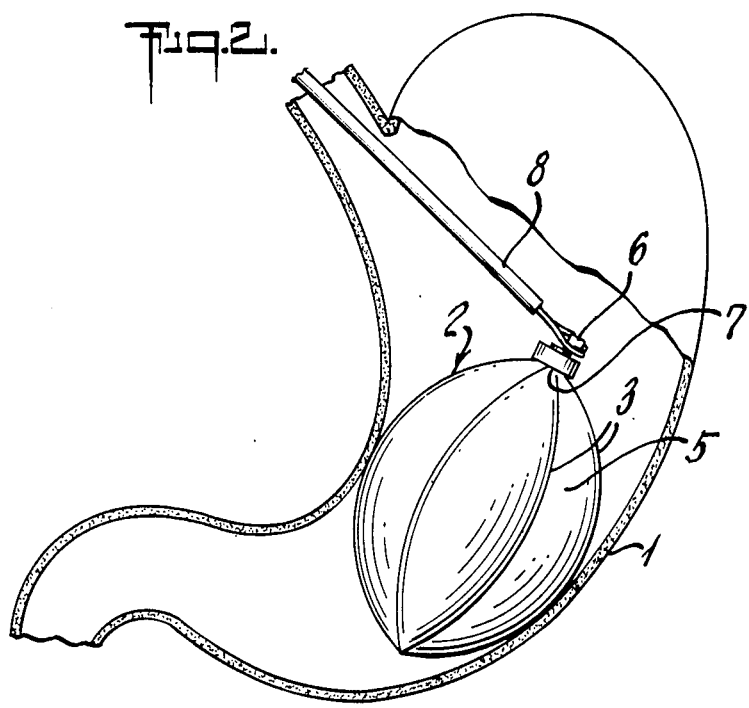
FIG. 2 is a schematic side view of an endoscope forceps or snare in the process of grasping and positioning the balloon within the stomach, as might be necessary prior to puncturing the balloon for endoscopic removal from the stomach.

As best shown in FIG. 2, a small tag of plastic 6 at the self-sealing hole end may be held by an endoscopic forceps 8 or snare for positioning. The entire device is made flexible enough and narrow enough to easily pass through the small bowel if accidentally or intentionally deflated.

FIG. 3 best illustrates a front view of the balloon fully inflated. A partial cross-section view 10 illustrates the thin film from which the balloon is constructed. Representative dimensions are:

$R_3$, the distance between the central longitudinal axis and the outermost part of the lobe, equal to 4.0 cm;

$R_4$, the radius of curvature of the outside surface of the lobe, equal to 1.8 cm.;

$R_5$, the radius of the outer ring of the inflation valve, equal to 0.5 cm.;

Q, the distance between the axes of curvature of opposing lobes, equal to 4.8 cm.;

H, the distance between the surfaces of opposing lobes, equal to 8.0 cm.

FIG. 5 best illustrates a plan view of the balloon fully inflated. Representative dimensions are:

L, the long axis, equal to 10.8 cm.;

$R_2$, the radius of curvature of the apex of a lobe, equal to 5.9 cm.;

$R_1$, the radius of curvature of the lateral edge of a lobe viewed in plan projection, equal to 9.3 cm.

In one currently preferred method of introducing the balloon to a human stomach, the deflated balloon is loaded into the distal end of an orogastric tube, the balloon air port having been loaded with the needle device for instillation of air and the proximal end of this device emerging from the proximal end of the orogastric tube, and being attached to a suitable source of pressurized air. A pusher device, viz. a flexible rod, is also provided in the orogastric tube. Once the preloaded orogastric tube is inserted into the stomach, the balloon is pushed out of the distal end of the tube (by means of the rod) and inflated. Following inflation, the orogastric tube, pusher device and needle device are all removed, leaving the inflated balloon in place.

It is to be understood that the invention is not limited to the features and embodiments hereinabove specifically set forth, but may be carried out in other ways without departure from its spirit.

We claim:

1. A flexible-walled, imperforate, air-inflatable balloon insertable and inflatable within the stomach of a human or animal to deter ingestion of food by occupying a substantial portion of the stomach volume, wherein the improvement comprises:
    (a) said balloon having a plurality of wall portions that form smooth-surfaced convex outward protrusions when inflated,
    (b) said protrusions being distributed around the balloon and cooperatively defining a plurality of outwardly open channels for passage of fluent material between the balloon outer surface and the stomach wall, and
    (c) said protrusions being shaped and disposed to permit engagement of the stomach wall by the balloon only at spaced localities so as to maintain a substantial portion of the stomach wall away from contact with the balloon, for minimizing complications due to mechanical trauma of the balloon against the stomach wall.

2. A balloon as defined in claim 1, wherein said protrusions are shaped to engage the stomach wall substantially only tangentially and to maintain the stomach wall away from contact with the balloon surface except at localities of tangential engagement of the stomach wall by said protrusions.

3. A balloon as defined in claim 1, wherein each of said protrusions is a lobe extending longitudinally between first and second diametrically opposed localities on the inflated balloon, and wherein said channels are valleys defined between adjacent lobes.

4. A balloon as defined in claim 3, having a generally elongated shape, wherein each said lobe extends lengthwise of the balloon.

5. A balloon as defined in claim 3, wherein said protrusions are distributed substantially uniformly around an axis of the balloon extending between said diametrically spaced localities and are substantially identical in dimension and configuration.

6. A balloon as defined in claim 5, wherein each said protrusion tapers toward each of said diametrically spaced localities.

7. A balloon as defined in claim 5, wherein there are four of said protrusions disposed 90° apart around said axis.

8. A balloon as defined in claim 1, wherein there is at one end a self-sealing hole through which a hollow pin can be introduced, the pin being constructed so as to be compatible with air delivery through the main "air" port on a standard upper endoscope.

9. A balloon as defined in claim 8, wherein a tag of plastic is attached so it can be held by a standard endoscopic biopsy forceps.

10. A method of treating a human or animal having a stomach to deter ingestion of food, comprising inserting and inflating within the stomach a flexible walled, imperforate, air-inflatable balloon dimensioned to occupy a substantial part of the stomach volume and having a plurality of wall portions that form smooth-surfaced convex outward protrusions when inflated, said protrusions being distributed around the balloon and cooperatively defining a plurality of outwardly open channels for passage of fluent material between the balloon outer surface and the stomach wall, and said protrusions being shaped and disposed to permit engagement of the stomach wall by the balloon only at spaced localities so as to maintain a substantial portion of the stomach wall away from contact with the balloon, for minimizing complications due to mechanical trauma of the balloon against the stomach wall.

* * * * *